US00PP34823P3

(12) United States Plant Patent
Olesen et al.

(10) Patent No.: US PP34,823 P3
(45) Date of Patent: Dec. 13, 2022

(54) ***CLEMATIS* PLANT NAMED 'EVIPO106'**

(50) Latin Name: *Clematis viticella*
Varietal Denomination: Evipo106

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,631

(22) Filed: Sep. 7, 2021

(65) Prior Publication Data

US 2022/0095517 P1 Mar. 24, 2022

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72
See application file for complete search history.

(56) References Cited

PUBLICATIONS

CPVO Application Consultation, QZ PBR 20202279 filed Sep. 22, 2020 for a *Clematis* plant named, 'EVIPO106', downloaded from https://online.plantvarieties.eu/publicConsultationDetails?registerId=20202279&denomination=evipo106.*

* cited by examiner

*Primary Examiner* — Anne Marie Grunberg

(57) ABSTRACT

A new *Clematis* plant with a compact growth habit, profuse, pink flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification:
Genus: *Clematis.*
Species: *viticella.*
Variety denomination: 'Evipo106'.

This application claims priority to Plant Breeder's Rights Application Number 2020/2279, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo106' originated as a single seedling from the stated cross.

The new *Clematis* plant may be distinguished from its female seed parent and male pollen parent by the following characteristics. The female seed parent grows to 100 cm in one season while the new variety is very compact, and grows up to 20 cm in one season. The male seed parent has purple tepals, while the new variety has pink tepals.

The objective of the hybridization of this *Clematis* plant was to create a new and distinct variety for nursery culture with unique qualities such as:

1. Uniform and abundant pink flowers;
2. Ultra-compact growth, making the variety suitable for a variety of container culture uses; and
3. Improved disease resistance.

This combination of qualities was lacking in *Clematis* plants that were in commercial cultivation and the qualities have been substantially achieved in the new variety.

'Evipo106' was selected by Mogens N. Olesen and Raymond J. Evison in their *Clematis* development program in the Channel Islands, United Kingdom in 2008. Asexual reproduction of 'Evipo106' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo106' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo106'.

Specifically illustrated in FIG. 1 of the drawings shows an open flowers and buds at various stages of opening, flower viewed from above and underneath, reproductive flower parts, and tepals detached.

Figure 1:
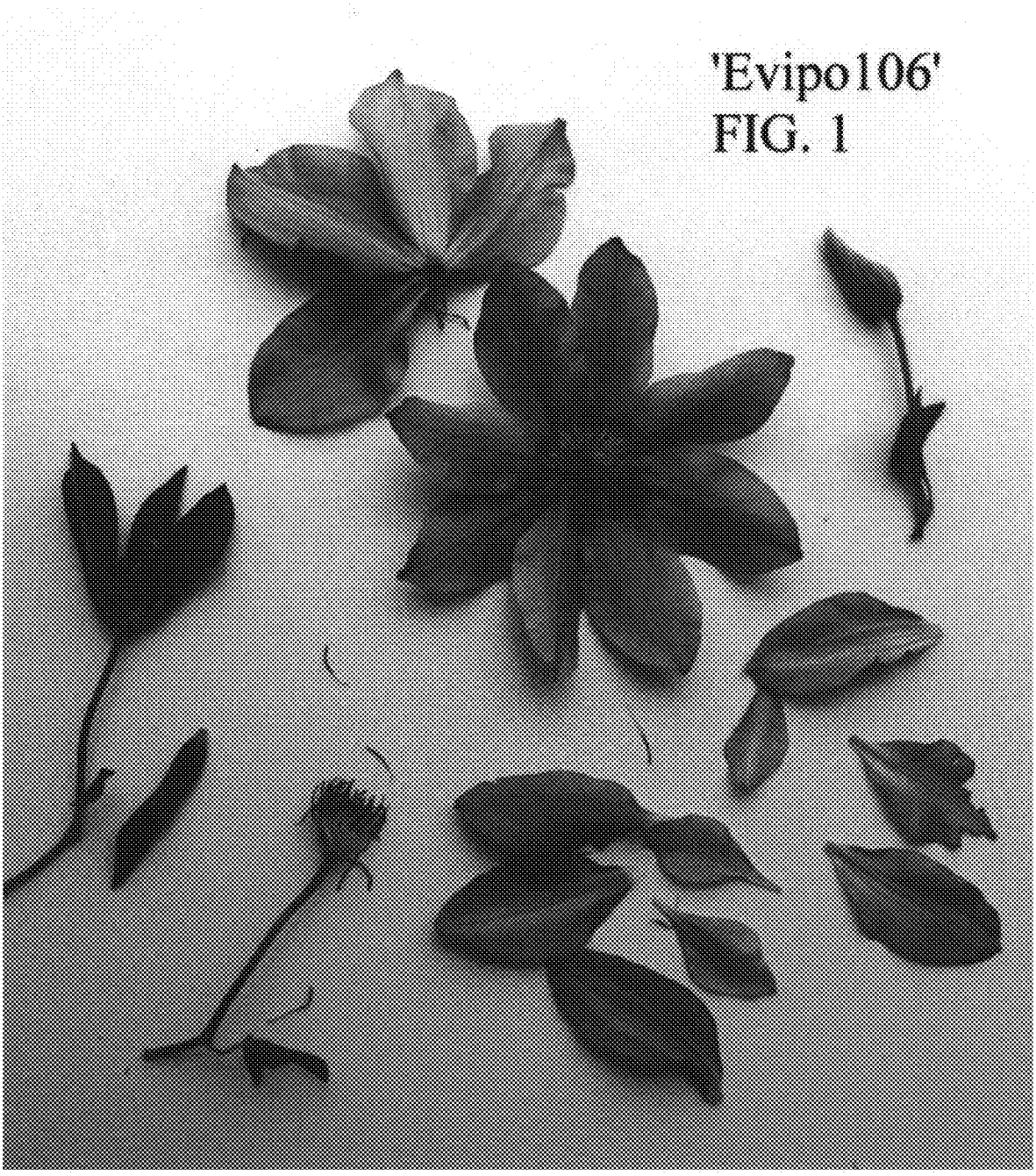
Figure 2:
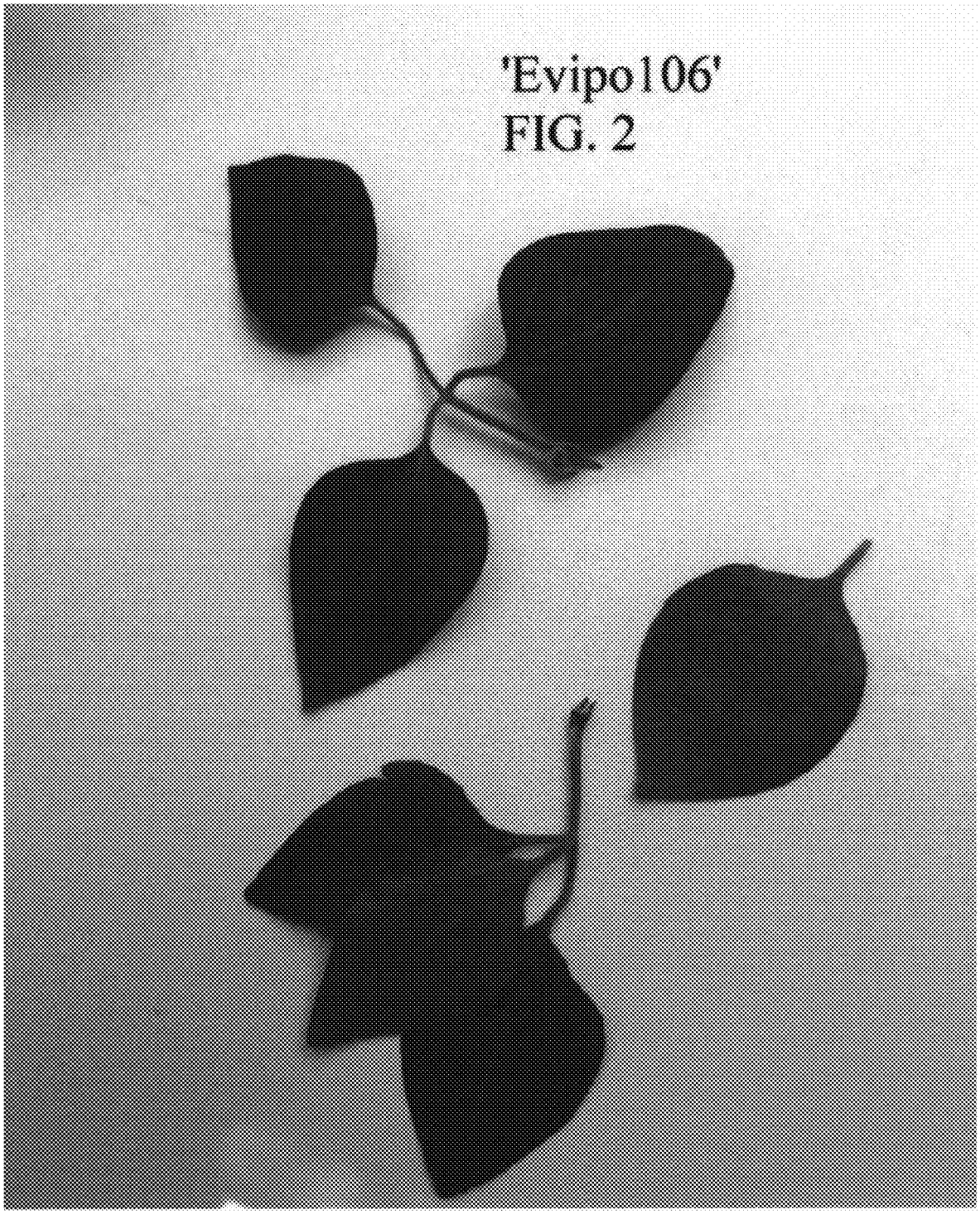
FIG. 2 shows mature leaves.
Figure 3:
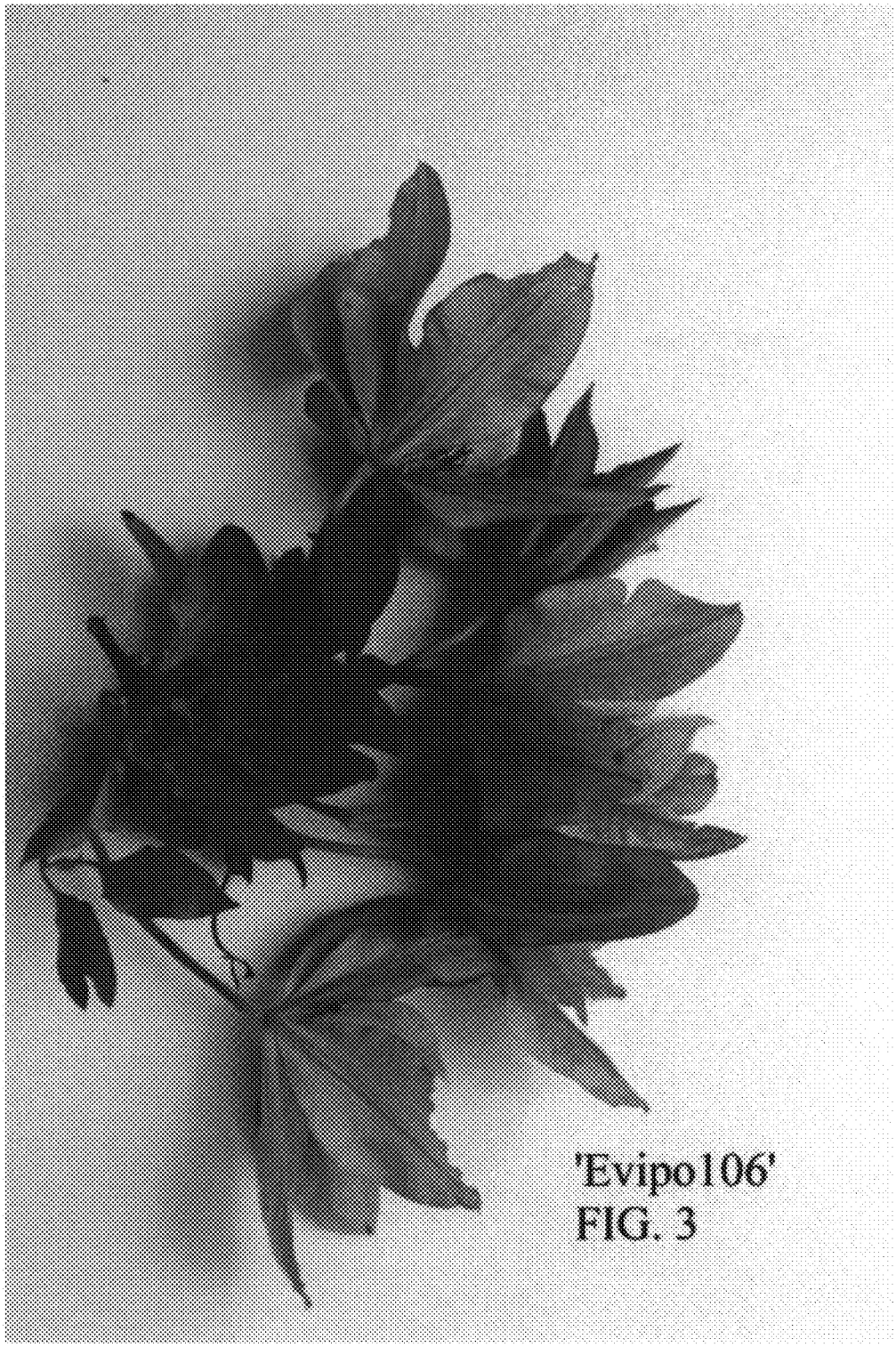
FIG. 3 shows a flowering branch.

Illustrated plants are 2 years of age.

DETAILED DESCRIPTION OF THE VARIETY

The following is a detailed description of 'Evipo106', as observed in its growth outdoor, throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo027' described and illustrated in U.S. Plant Pat. No. 27,281 are compared to 'Evipo106' in Chart 1.

CHART 1

| | 'Evipo106' | 'Evipo027' |
|---|---|---|
| Flower diameter | 130 mm | 145 mm |
| Tepal upper surface | Red-Purple Group 60A | Red-Purple Group 70 B with central bar Red-Purple Group 71A and 71B |
| Tepal count | 8 | 6 to 8 |

FLOWER AND FLOWER BUD

Blooming habit: Continuous. The natural flowering period is generally from April to September.

Flower bud:

*Size*.—Normally 35 mm in length. Bud diameter is 14 mm.

*Bud form*.—Long campanulate, broad based.

*Bud color*.—Yellow-Green Group 144A with intonations of Greyed-Orange Group 177B.

*Texture*.—Pubescent.

Pedicel:

*Surface texture*.—Smooth.

*Length*.—On average 54 mm in length with 3 mm diameter.

*Color*.—Yellow-Green Group 144A.

*Strength*.—Moderately strong.

Receptacle:

*Surface texture*.—Lightly pubescent.

*Shape*.—Broad funnel.

*Size*.—1.5 mm (h)×7 mm (w).

*Color*.—Yellow-Green Group 144A.

Flower arrangement:

*Location on vine*.—New growth only.

Normally in clusters of: Three to seven flowers.

Flower bloom:

*Size*.—On average, 130 mm in diameter and 25 mm in depth.

*Profile*.—Open flowers are flat.

*Fragrance*.—None.

*Lasting quality*.—Flowers normally remain up to 15 days on the plant.

Tepals:

*Tepal color*.—Upon opening, the upper surface is Red-Purple Group 60A. The lower surface is Purple Group 77B. After opening, the upper surface is Purple Group N79D at the mid line, margins are Violet Group 84C. The lower surface is Red-Purple Group 76B with marginal intonations of Red-Purple Group 72B.

*Quantity*.—Normally 8 tepals.

*Size*.—Average 70 mm in length by 31 mm wide.

*Shape*.—Individual tepals are spatulate. The tepal apex is acute. The tepal base is attenuate.

*Apex recurvature*.—Flat.

*Tepal cross section*.—Flat.

*Margins*.—Entire. Long slight undulations.

*Persistence*.—Tepals will drop off cleanly.

Reproductive organs:

*Pollen*.—None observed.

*Anthers*.—Size: 6 to 7 mm in length. Color: Greyed-Purple Group 183B and Black Group 202A. Quantity: On average, 60.

*Filaments*.—Color: Green-White Group 157B. Length: 6 mm.

*Pistils*.—Quantity: On average, 30.

*Stigmas*.—Inferior in location relative to the length of the filaments and the height of the anthers.

*Styles*.—Color: Green-White Group 157B. Length: 11 mm.

Seed head characteristics: Seed not observed to date.

PLANT

Plant form: Mounding, very compact.

Plant growth: Moderately vigorous.

Size: Seasons growth attains 15 to 20 cm in height. Average spread is 30 cm.

Stems:

*Color*.—Juvenile stems are Yellow-Green Group 144A.

*Internodes*.—On average, 10 to 15 mm between nodes.

*Length*.—Normally 5 cm from the base of the plant to the flowering portion of the stem.

*Diameter*.—About 3.5 to 4 mm.

*Texture*.—Smooth.

Plant foliage:

*Leaf characteristics*.—Deciduous.

*Arrangement*.—Trifoliate.

*Leaf size*.—Compound leaves are about 96 mm (l)×120 mm (w). Leaflets are about 45 mm (l)×35 mm (w).

*Abundance*.—On average 5 leaves per 10 cm of stem.

*Leaf color*.—Mature upper Green Group 137A. Mature lower Yellow-Green Group 146B.

*Stipules*.—Absent.

*Petioles*.—Size: Normally 26 mm in length by 1.5 mm diameter. Texture: Smooth. Color: Yellow-Green Group 144A.

*Petioloule*.—Size: About 15 mm in length by 1.5 mm diameter. Texture: Smooth. Color: Yellow-Green Group 144A.

*Leaflet shape*.—Cordate. The base is rounded, apex broadly acuminate.

*Margin*.—Entire.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo106', substantially as described and illustrated , due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo106'

'Evipo106'

'Evipo106'